US011432920B2

(12) United States Patent
Berry et al.

(10) Patent No.: US 11,432,920 B2
(45) Date of Patent: Sep. 6, 2022

(54) SYSTEMS AND METHODS OF PREPARING A GRAFT

(71) Applicant: Genesis Biologics, Inc., Anaheim, CA (US)

(72) Inventors: Robert J. Berry, Laguna Niguel, CA (US); Steven T. Bee, San Diego, CA (US)

(73) Assignee: Genesis Biologics, Inc., Anaheim, CA (US)

( * ) Notice: Subject to any disclaimer, the term of this patent is extended or adjusted under 35 U.S.C. 154(b) by 0 days.

(21) Appl. No.: 16/646,542

(22) PCT Filed: Nov. 13, 2019

(86) PCT No.: PCT/US2019/061299
§ 371 (c)(1),
(2) Date: Mar. 11, 2020

(87) PCT Pub. No.: WO2020/102438
PCT Pub. Date: May 22, 2020

(65) Prior Publication Data
US 2021/0212809 A1 Jul. 15, 2021

Related U.S. Application Data

(60) Provisional application No. 62/760,806, filed on Nov. 13, 2018.

(51) Int. Cl.
*A61F 2/08* (2006.01)

(52) U.S. Cl.
CPC ..... *A61F 2/0811* (2013.01); *A61F 2002/0852* (2013.01); *A61F 2220/0075* (2013.01)

(58) Field of Classification Search
CPC ................................ A61F 2/68; A61B 17/00
See application file for complete search history.

(56) References Cited

U.S. PATENT DOCUMENTS

| | | | |
|---|---|---|---|
| 6,203,572 B1 | 3/2001 | Johnson et al. | |
| 8,298,284 B2 * | 10/2012 | Cassani | A61F 2/08 623/13.14 |
| 10,959,829 B2 * | 3/2021 | Snedeker | A61F 2/0811 |
| 2002/0173849 A1 | 11/2002 | McKernan et al. | |
| 2006/0157066 A1 * | 7/2006 | Moore | A61F 2/26 128/898 |
| 2010/0121450 A1 | 5/2010 | Hart | |

(Continued)

FOREIGN PATENT DOCUMENTS

| EP | 1013239 A2 | 6/2000 |
|---|---|---|
| WO | 2016/113142 A1 | 7/2016 |

OTHER PUBLICATIONS

Extended European Search Report issued with corresponding European Patent Application No. 19884702.2 dated Jul. 21, 2022.

*Primary Examiner* — Yashita Sharma
(74) *Attorney, Agent, or Firm* — Troutman Pepper Hamilton Sanders LLP

(57) ABSTRACT

The present disclosure relates generally to methods for preparing a graft with at least two implants of biocompatible materials, the graft being folded a plurality of times prior to being used in reconstructing a treatment site. Methods of this disclosure are contemplated for preparing a graft at a site outside of a hospital setting, storing offsite, and/or later transporting to the hospital for use with a patient.

20 Claims, 20 Drawing Sheets

(56) References Cited

U.S. PATENT DOCUMENTS

| | | |
|---|---|---|
| 2010/0256677 A1 | 10/2010 | Albertorio et al. |
| 2010/0274355 A1 | 10/2010 | McGuire et al. |
| 2011/0282447 A1* | 11/2011 | Niu ..................... A61F 2/0805 |
| | | 623/13.11 |
| 2013/0096612 A1 | 4/2013 | Zajac et al. |
| 2014/0243976 A1 | 8/2014 | Schmieding et al. |
| 2014/0257346 A1* | 9/2014 | Sengun ............. A61B 17/0401 |
| | | 606/148 |
| 2019/0274809 A1* | 9/2019 | Kapec .................. B65D 75/326 |

\* cited by examiner

1900 →

| | |
|---|---|
| SUTURING THE FIRST PROXIMAL END AND SUTURING THE FIRST DISTAL END | 1905 |

↓

| | |
|---|---|
| POSITIONING A FIRST IMPLANT BETWEEN THE FIRST PROXIMAL AND FIRST DISTAL ENDS, THE FIRST IMPLANT COMPRISING A LOOP ORIENTED ABOUT THE GRAFT BETWEEN THE PROXIMAL AND DISTAL ENDS | 1910 |

↓

| | |
|---|---|
| FOLDING THE FIRST DISTAL OR FIRST PROXIMAL END OF THE GRAFT ABOUT THE LOOP OF THE FIRST IMPLANT UNTIL THE FIRST DISTAL OR PROXIMAL END ARE IN CONTACT OR ADJACENT THE OTHER OF THE ENDS, WHEREIN A SECOND PROXIMAL END AND A SECOND DISTAL END ARE NOW FORMED BY THE FOLDING OF THE GRAFT, THE SECOND PROXIMAL END BEING ADJACENT THE FIRST PROXIMAL AND DISTAL ENDS | 1915 |

↓

| | |
|---|---|
| POSITIONING A SECOND IMPLANT BETWEEN THE SECOND PROXIMAL AND SECOND DISTAL ENDS, THE SECOND IMPLANT COMPRISING A LOOP ORIENTED ABOUT THE GRAFT BETWEEN THE SECOND PROXIMAL AND DISTAL ENDS | 1920 |

↓

| | |
|---|---|
| FOLDING THE SECOND DISTAL END OF THE GRAFT ABOUT THE LOOP OF THE SECOND IMPLANT UNTIL THE SECOND DISTAL END CONTACTS OR IS ADJACENT THE FIRST PROXIMAL AND/OR DISTAL END | 1925 |

↓

| | |
|---|---|
| MOVING THE SECOND DISTAL END AWAY THE FIRST PROXIMAL AND/OR DISTAL END | 1930 |

↓

| | |
|---|---|
| DISTALLY MOVING THE FIRST IMPLANT TOWARDS THE SECOND IMPLANT AND ORIENTING DOWNWARD THE LOOP OF THE FIRST IMPLANT, THE FIRST IMPLANT BEING DISTALLY MOVED BETWEEN FOLDED SEGMENTS OF THE GRAFT | 1935 |

↓

| | |
|---|---|
| STITCHING AND/OR SUTURING PORTIONS OF SECOND PROXIMAL AND/OR DISTAL ENDS TOGETHER | 1940 |

Fig. 19

SYSTEMS AND METHODS OF PREPARING A GRAFT

CROSS-REFERENCE TO RELATED APPLICATIONS

This application is a United States national stage entry of International Patent Application No. PCT/US2019/061299 filed Nov. 13, 2019, which claims priority to U.S. Provisional Application Ser. No. 62/760,806, filed on Nov. 13, 2018, the contents of which are incorporated into this application by reference in their entirety as if set forth verbatim.

FIELD

This present disclosure relates methods for preparing grafts for ligament reconstruction.

BACKGROUND

Tissue grafts for ligament reconstruction are common in modern medical practice. In order to insert the tissue graft into a joint, substantial time is required to prepare the graft. Current procedures normally can last 30 minutes in the operating room or in the hospital for the suturing of the graft prior to insertion which takes considerable time and resources in the operating room. Such procedures are also known to be prone to error or even lead to infection if done improperly.

It is an object of this disclosure to eliminate the need for using such resources in the surgical setting or in the operating room thereby reducing hospital resources and human error. Another object of the present disclosure is to provide a device and method which is economical and simple to use. The solution of this disclosure resolves these and other issues of the art.

SUMMARY

Disclosed herein are various exemplary devices, systems, and methods of the present disclosure that can address the above needs. In some embodiments, a method for preparing a graft for a patient at a location that is separate from an operating room or a hospital. The method can include suturing the first proximal end and suturing the first distal end; positioning a first implant between the first proximal and first distal ends, the first implant comprising a loop oriented about the graft between the proximal and distal ends; then folding the first distal or first proximal end of the graft about the loop of the first implant until the first distal or proximal end are in contact or adjacent the other of the ends, wherein a second proximal end and a second distal end are now formed by the folding of the graft, the second proximal end being adjacent the first proximal and distal ends; then positioning a second implant between the second proximal and second distal ends, the second implant comprising a loop oriented about the graft between the second proximal and distal ends; then folding the second distal end of the graft about the loop of the second implant until the second distal end contacts or is adjacent the first proximal and/or distal end; then moving the second distal end away from the first proximal and/or distal end; then distally moving the first implant towards the second implant and orienting downward the loop of the first implant, the first implant being distally moved between folded segments of the graft; then stitching and/or suturing portions of second proximal and/or distal ends together.

In some examples, the method includes then transporting the prepared graft to a hospital.

In some examples, the method includes administering cephalexin to the patient; and then reconstructing a treatment site of interest of a patient with the prepared graft. It is understood that cephalexin is an antibacterial drug intended for oral administration that is 7-(D-α-Amino-α-phenylacetamido)-3-methyl-3-cephem-4-carboxylic acid monohydrate. Cephalexin has the molecular formula $C_{16}H_{17}N_3O_4S \cdot H_2O$.

In some examples, the cephalexin is orally administered using a capsule equivalent to 250 mg cephalexin.

In some examples, the cephalexin is orally administered using a capsule equivalent to 500 mg cephalexin.

In some examples, the cephalexin is orally administered using a capsule equivalent to 700 mg cephalexin.

In some examples, the method includes administering Keflex, ancef via intravenous therapy, and/or Clindamycin in connection with reconstruction of the treatment site of the patient using the prepared graft.

In some examples, the method includes then reconstructing a treatment site of interest of a patient with the prepared graft, such as the anterior cruciate ligament, medial collateral ligament, posterior cruciate ligament, or the like.

In some examples, a step of providing the graft relates to one or more tendons from the semitendinosus, gracilis, anterior tibialis, posterior tibialis, or the peroneus longus.

In some examples, the step of suturing the first proximal end and suturing the first distal end is implemented using the Krackow method.

In some examples, the step of suturing the first proximal end and suturing the first distal end is implemented using suture(s) and/or suture tape of 1.5 mm and/or 2.0 mm.

In some examples, the step of moving the second distal end away from the first proximal and/or distal end is implemented by pivoting the second distal end about a pivot point between the second distal end and the first proximal and/or distal end.

In some examples, the step of moving the second distal end away from the first proximal and/or distal end is implemented by pivoting the second distal end a predetermined distance away from the first proximal and/or distal end, the predetermined distance being greater than a width or thickness of the first implant.

In some examples, the first and second implants comprise one or more durable elongate ropes constructed from a high tension biocompatible material. The material can include one or more of ultra-high-molecular-weight polyethylene (UHMWPE), Polypropylene (PP), with coating, without coating, lubricated, non-lubricated, single filament, multi-filament, and the like.

In some examples, the step of orienting downward the loop of the first implant includes reorienting the first implant at least 90 degrees until being positioned by having its loop angled substantially downward.

In some examples, the step of stitching and/or suturing portions of second proximal and/or distal ends together comprises implanting at least five half-stiches.

In some examples, the graft measures 230 mm-260 mm length by 8.5 mm-10.0 mm.

In some examples, a graft is disclosed and prepared according to any of the herein disclosed methods, wherein the first and second implants of said graft have one or more durable elongate ropes constructed from a biocompatible material.

In some examples, a graft is disclosed and prepared according to any method as shown and described herein and can include each and every novel feature or combination of features disclosed herein.

In some examples, a graft is disclosed prepared by folding said graft twice onto itself and interweaving an implant at opposing distal and proximal ends of said double folded graft.

In some examples, the implant is constructed from a high tension biocompatible material.

In some examples, the graft relates to one or more tendons from the semitendinosus.

In some examples, the graft relates to one or more tendons from the gracilis.

In some examples, the graft relates to one or more tendons from the anterior tibialis.

In some examples, the graft relates to one or more tendons from the posterior tibialis.

In some examples, the graft relates to one or more tendons from the peroneus longus.

In some examples, use of a graft is disclosed that is prepared for a patient at a location that is separate from an operating room or a hospital. The use includes suturing a first proximal end and a first distal end of a tendon; positioning a first implant between the first proximal and first distal ends, the first implant comprising a loop oriented about the graft between the proximal and distal ends; then folding the first distal or first proximal end of the graft about the loop of the first implant until the first distal or proximal end are in contact or adjacent the other of the ends, wherein a second proximal end and a second distal end are now formed by the folding of the graft, the second proximal end being adjacent the first proximal and distal ends; then positioning a second implant between the second proximal and second distal ends, the second implant comprising a loop oriented about the graft between the second proximal and distal ends; then folding the second distal end of the graft about the loop of the second implant until the second distal end contacts or is adjacent the first proximal and/or distal end; then moving the second distal end away from the first proximal and/or distal end; then distally moving the first implant towards the second implant and orienting downward the loop of the first implant, the first implant being distally moved between folded segments of the graft; then stitching and/or suturing portions of second proximal and/or distal ends together; then transporting the prepared graft to a hospital; administering cephalexin to the patient; and then reconstructing a treatment site of interest of a patient with the prepared graft, such as the anterior cruciate ligament, medial collateral ligament, or the like.

In some examples, the cephalexin is orally administered using a capsule equivalent to 250 mg cephalexin.

In some examples, the cephalexin is orally administered using a capsule equivalent to 500 mg cephalexin.

In some examples, the cephalexin is orally administered using a capsule equivalent to 700 mg cephalexin.

In some examples, the method includes administering Keflex, ancef via intravenous therapy, and/or Clindamycin in connection with reconstruction of the treatment site of the patient using the prepared graft.

To the accomplishment of the foregoing and related ends, certain illustrative aspects are described herein in connection with the following description and the appended drawings. These aspects are indicative, however, of but a few of the various ways in which the principles of the claimed subject matter may be employed and the claimed subject matter is intended to include all such aspects and their equivalents. Other advantages and novel features may become apparent from the following detailed description when considered in conjunction with the drawings.

BRIEF DESCRIPTION OF THE DRAWINGS

The disclosure will be more clearly understood from the following description of some embodiments thereof, given by way of example only with reference to the accompanying drawings in which:

FIG. 19 depicts an example method of this disclosure.

DETAILED DESCRIPTION

Figure 1:
FIG. 1 depicts an example graft selection of this disclosure.

Although example embodiments of the present disclosure are explained in detail herein, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

In some cases, terms with commonly understood meanings are defined herein for clarity and/or for ready reference, and the inclusion of such definitions herein should not necessarily be construed to represent a substantial difference over what is generally understood in the art. All patents, applications, published applications and other publications referred to herein are incorporated by reference in their entirety. If a definition set forth in this section is contrary to or otherwise inconsistent with a definition set forth in the patents, application, published applications and other publications that are herein incorporated by reference, the definition set forth in this section prevails over the definition that is incorporated herein by reference.

As used herein, "a" or "an" means "at least one" or "one or more." As used herein, the term "user", "subject", "end-user" or the like is not limited to a specific entity or person. For example, the term "user" may refer to a person who uses the systems and methods described herein, and frequently may be a technician. However, this term is not limited to end users or technicians and thus encompasses a variety of persons or entities who can use the disclosed systems and methods.

As discussed herein, a "subject" may be any applicable human, animal, or other organism, living or dead, or other biological or molecular structure or chemical environment, and may relate to particular components of the subject, for instance specific tissues or tendons or ligaments.

As used herein, such a "biocompatible" component is one that is suitable for use with humans and/or animals without undue adverse side effects (such as toxicity, irritation, and allergic response) commensurate with a reasonable benefit/risk ratio.

As discussed herein, the terms "distal" or "proximal" are used in the following description with respect to a position or direction relative to opposed ends. For example, "distal" or "distally" can be a position distant from or in a direction away from one end, the physician, the interventionalist, etc. In contrast, "proximal" or "proximally" or "proximate" cane be a position opposite the distal and near or in a direction toward the patient or medical interventionist or any other point of reference.

A detailed description of aspects of the present disclosure will now be provided with reference to the accompanying drawings. The drawings form a part hereof and show, by way of illustration, specific embodiments or examples. In referring to the drawings, like numerals represent like elements throughout the several figures. As an example FIG. 1 depicts an example graft 10 of this disclosure at the beginning of the procedure. In particular, FIG. 1 depicts an example graft 10 that can pertain to one of the following tendons such as semitendinosus, gracilis, anterior tibialis, posterior tibialis, and the peroneus longus. Contemplated specifications for graft 10 can include 230 mm-260 mm length, 8.5 mm-10.0 mm that are folded at least more than four times diameter as discussed more particularly below.

Figure 2:
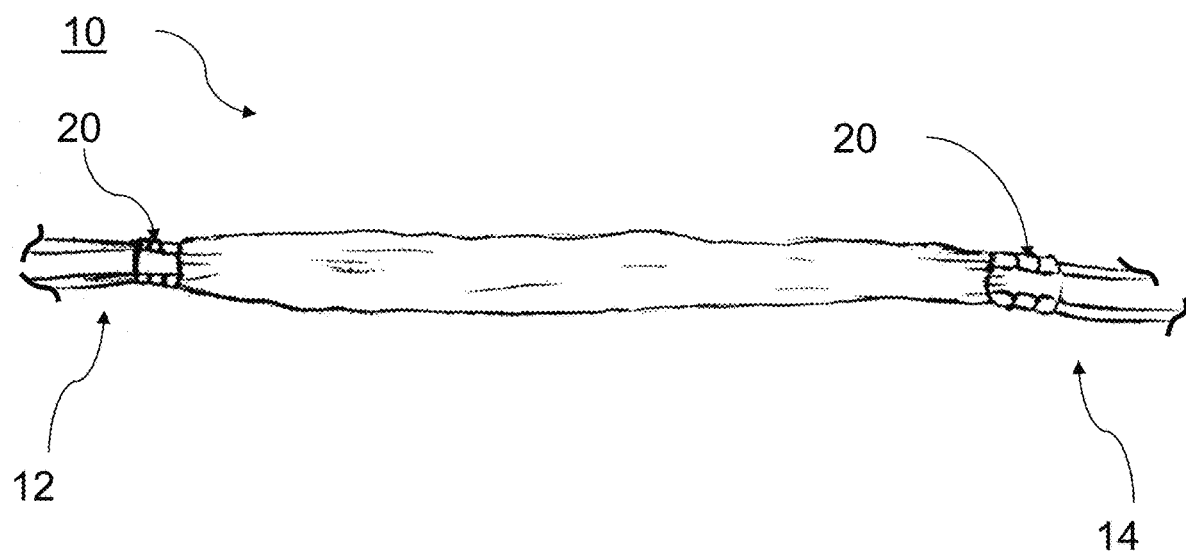
FIG. 2 depicts an example step of a method of this disclosure.

FIG. 2 depicts an example step of this disclosure. More specifically, graft 10 is shown with both proximal end 12 and distal end 14 sutured (e.g., a Krackow stitch method). In some examples, suture tape 20 is used with the step of FIG. 2, including suture tape of 1.5 mm, 2.0 mm, or the like.

Figure 3:
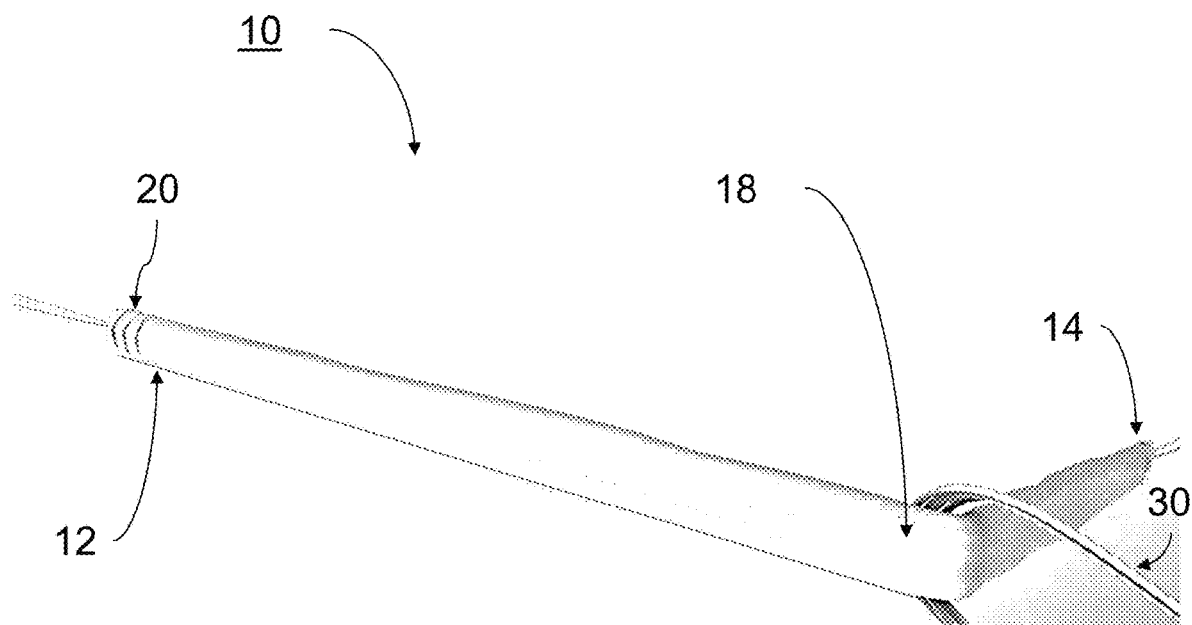
FIG. 3 depicts an example step of a method of this disclosure.
Figure 4:
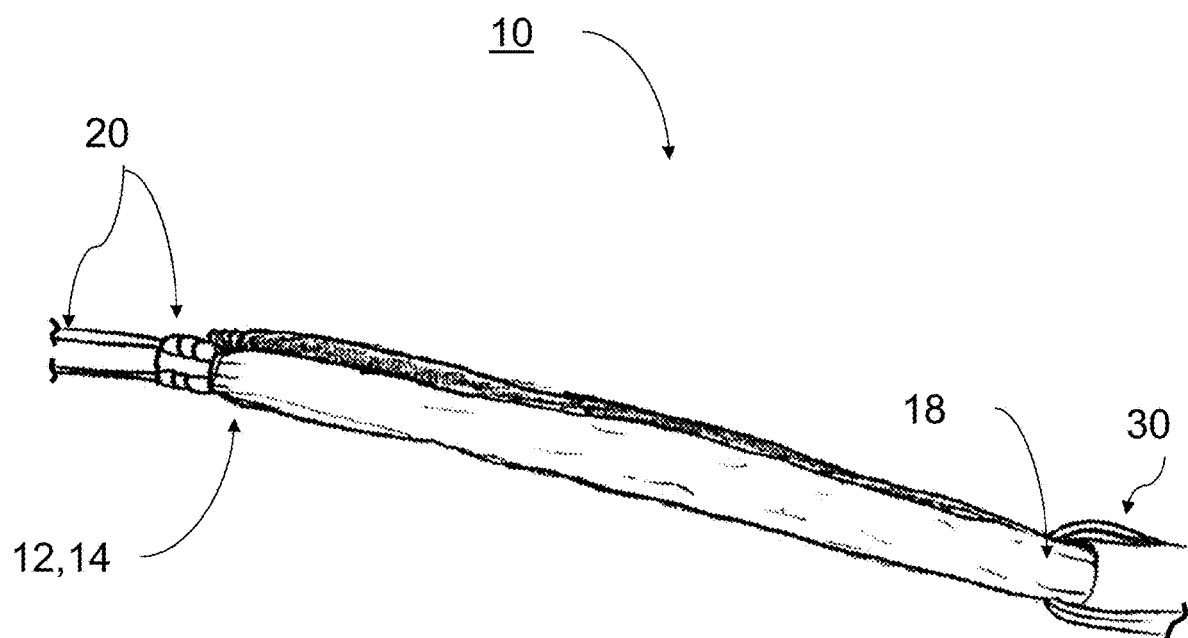
FIG. 4 depicts an example step of a method of this disclosure.

FIGS. 3-4 depict example steps of this disclosure following the step of FIG. 2. More specifically, graft 10 is shown being pivoted or otherwise moved so that graft 10 is folded in half. In some examples, graft 10 is folded by moving distal 14 or proximal 12 end of graft 10 about a central region 18 of graft 10 so that distal 14 and proximal 12 ends are adjacent or otherwise near the other. In turn, a first implant 30 is then positioned through, wrapped with, interwoven, or otherwise arranged with respect to the central region 18 of graft 10. It is understood that the term "implant" as used throughout this disclosure can mean durable elongate rope or high tension biocompatible material that can comply with applicable non-absorbable surgical standards. Materials contemplated for use with the "implants" of this disclosure include one or a combination of ultra-high-molecular-weight polyethylene (UHMWPE), Polypropylene (PP), with coating, without coating, lubricated, non-lubricated, single filament, multi-filament, and the like.

Figure 5:
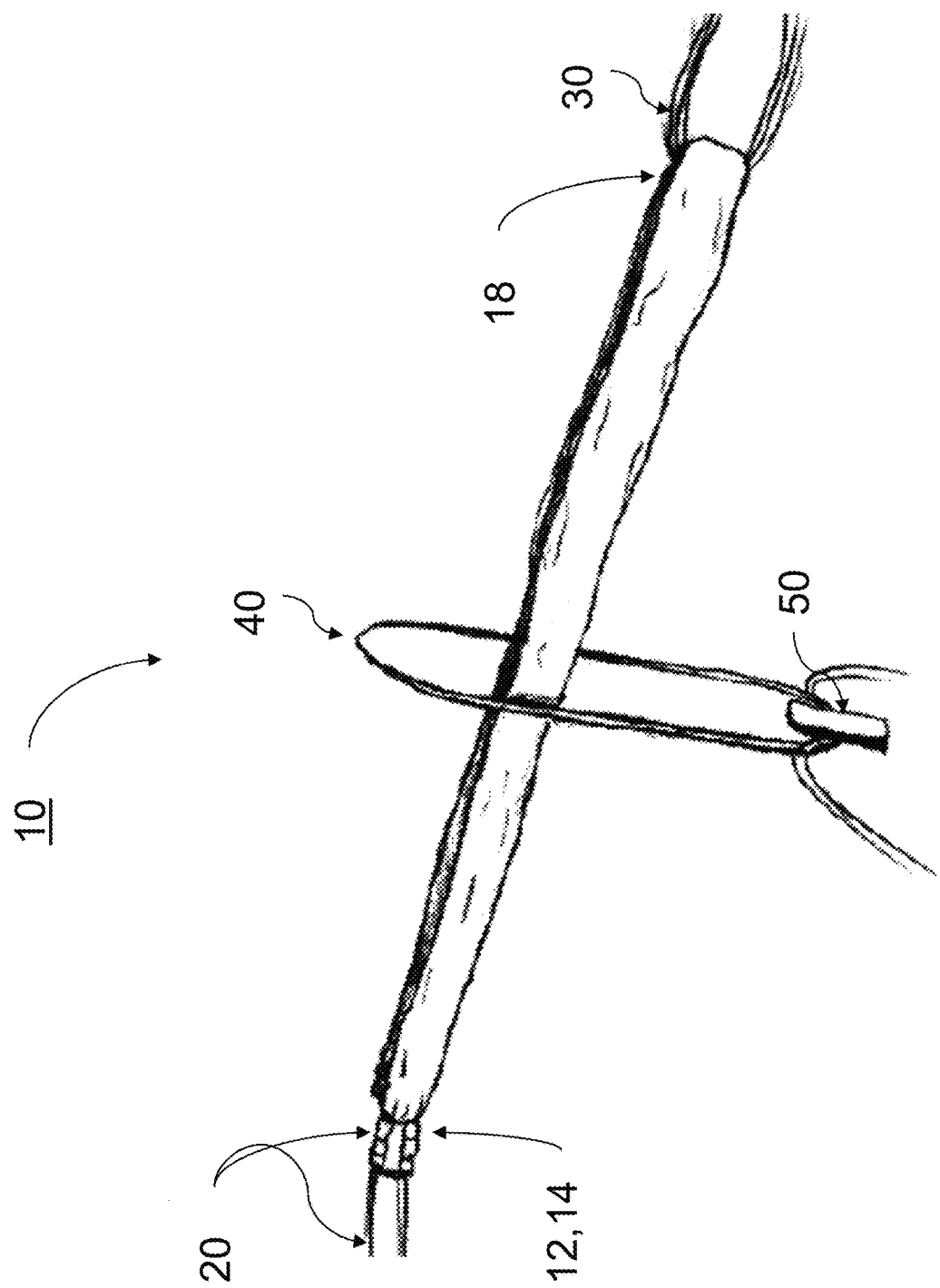
FIG. 5 depicts an example step of a method of this disclosure.

FIG. 5 depicts an example step of this disclosure following the step of FIG. 4. In particular, FIG. 5 depicts graft 10 with a second implant 40 arranged in a region of graft 10 between region 18 and ends 12, 14. Implant 40 can be positioned about a region of graft 10 between region 18 and ends 12, 14 by being looped (e.g., looped through one or more apertures or guides of fixation device 50) and translated distally from ends 12, 14 towards portion 18 until precisely positioned. Device 50 can be an implant that is constructed from a biocompatible, rigid material such as metal (e.g., titanium).

Figure 6:
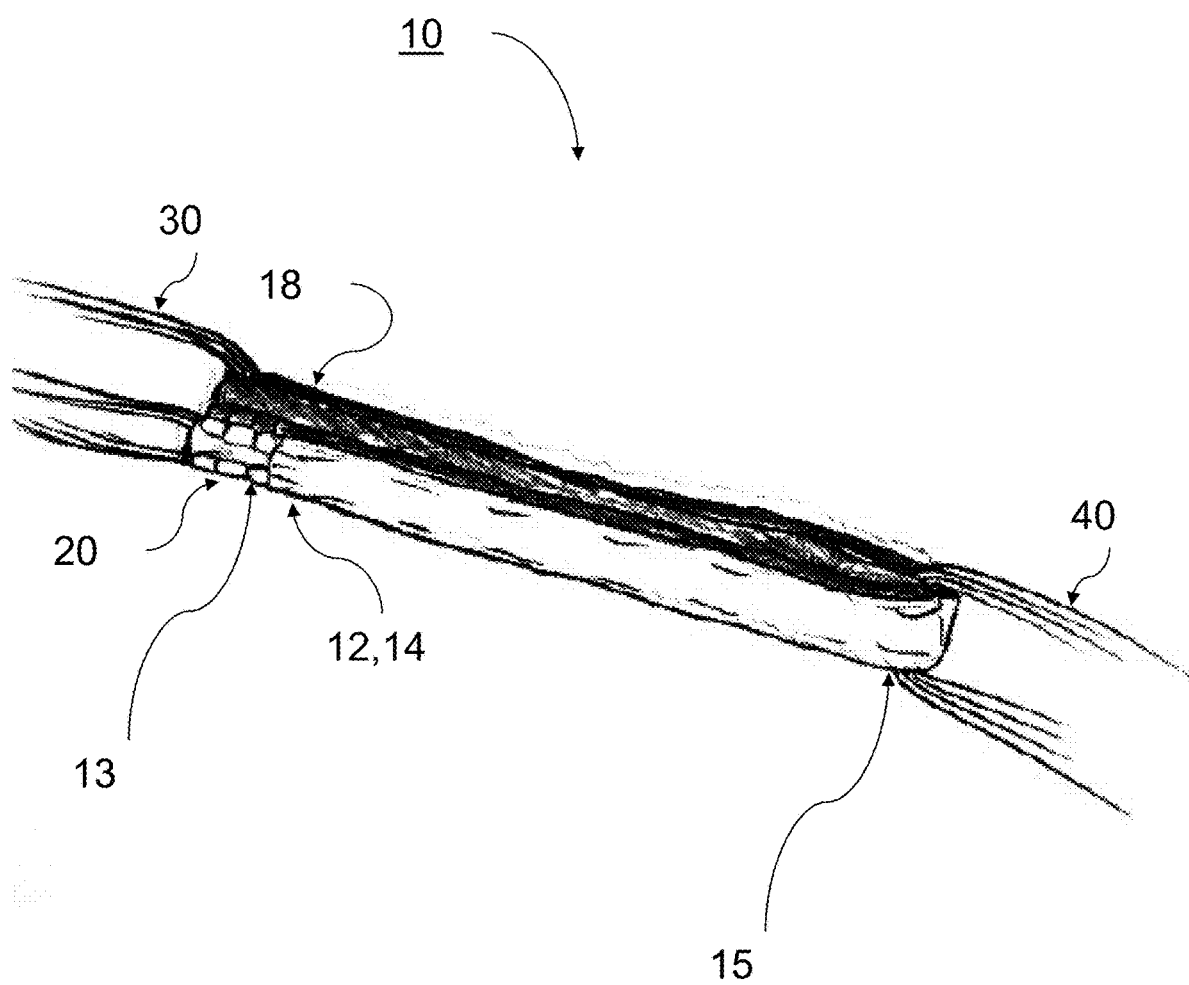
FIG. 6 depicts an example step of a method of this disclosure.

FIG. 6 depicts an example step of this disclosure following the step of FIG. 5. In particular, FIG. 6 depicts graft 10 having been folded once more about second implant 40 in the region of graft 10 between region 18 and ends 12, 14. Effectively, graft 10 has now been folded and arranged so that it has implants 30, 40 wrapped around or woven with each respective newly formed distal 15 and proximal 13 end of graft 10 and extended away from therefrom.

Figure 7:
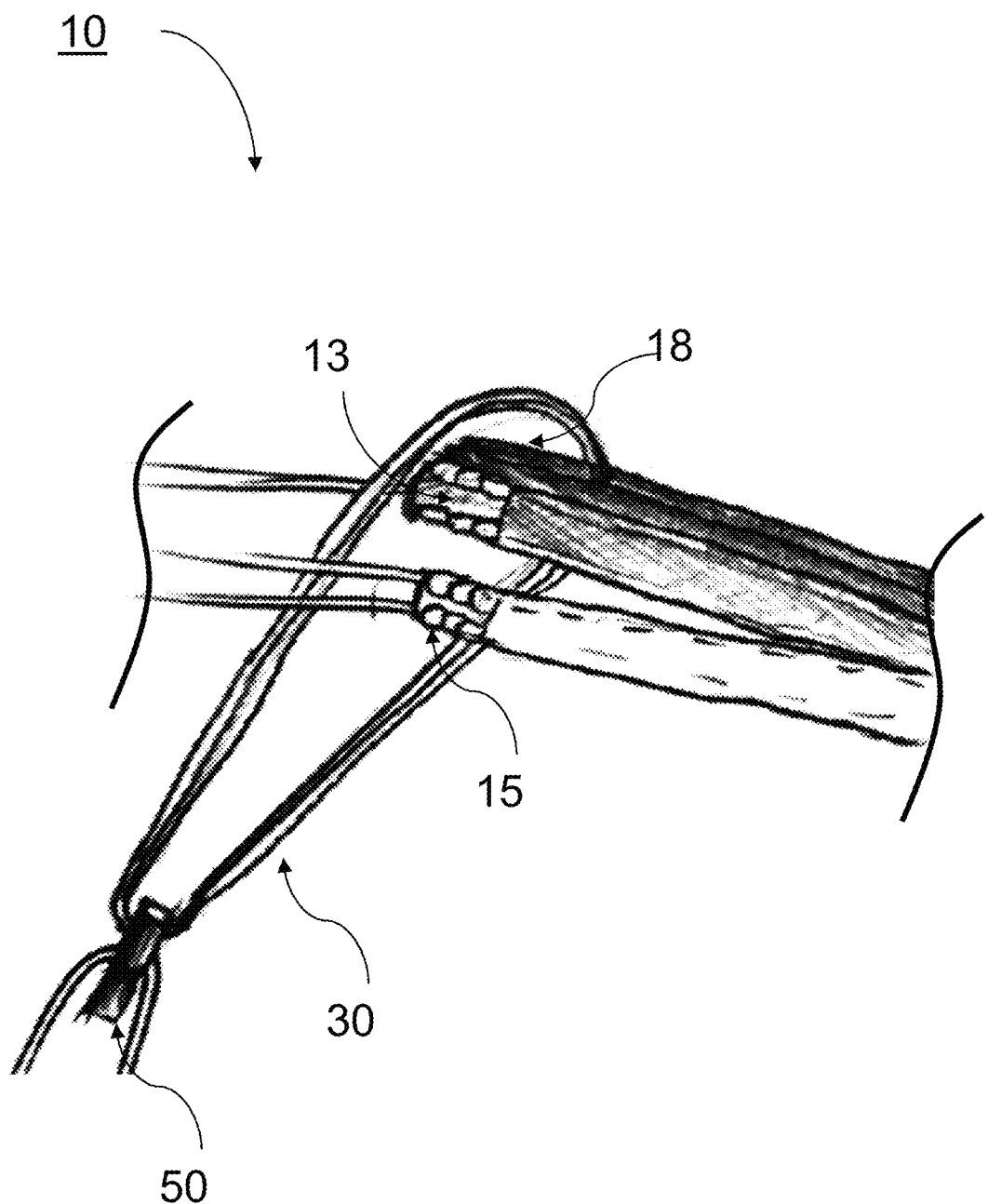
FIG. 7 depicts an example step of a method of this disclosure.

FIG. 7 depicts an example step of this disclosure following the step of FIG. 6. In particular, FIG. 7 shows end 15 being opened away from end 13 (e.g., pivoted about a point between respective ends of graft 10 and/or moved generally away) so implant 30 can be rotated or re-oriented downward and then inserted or otherwise woven between ends 13 and 15. Then, implant 30 can be distally moved towards implant 40 (not shown in FIG. 7). As shown, implant 30 can also be looped through device 50.

Figure 8:
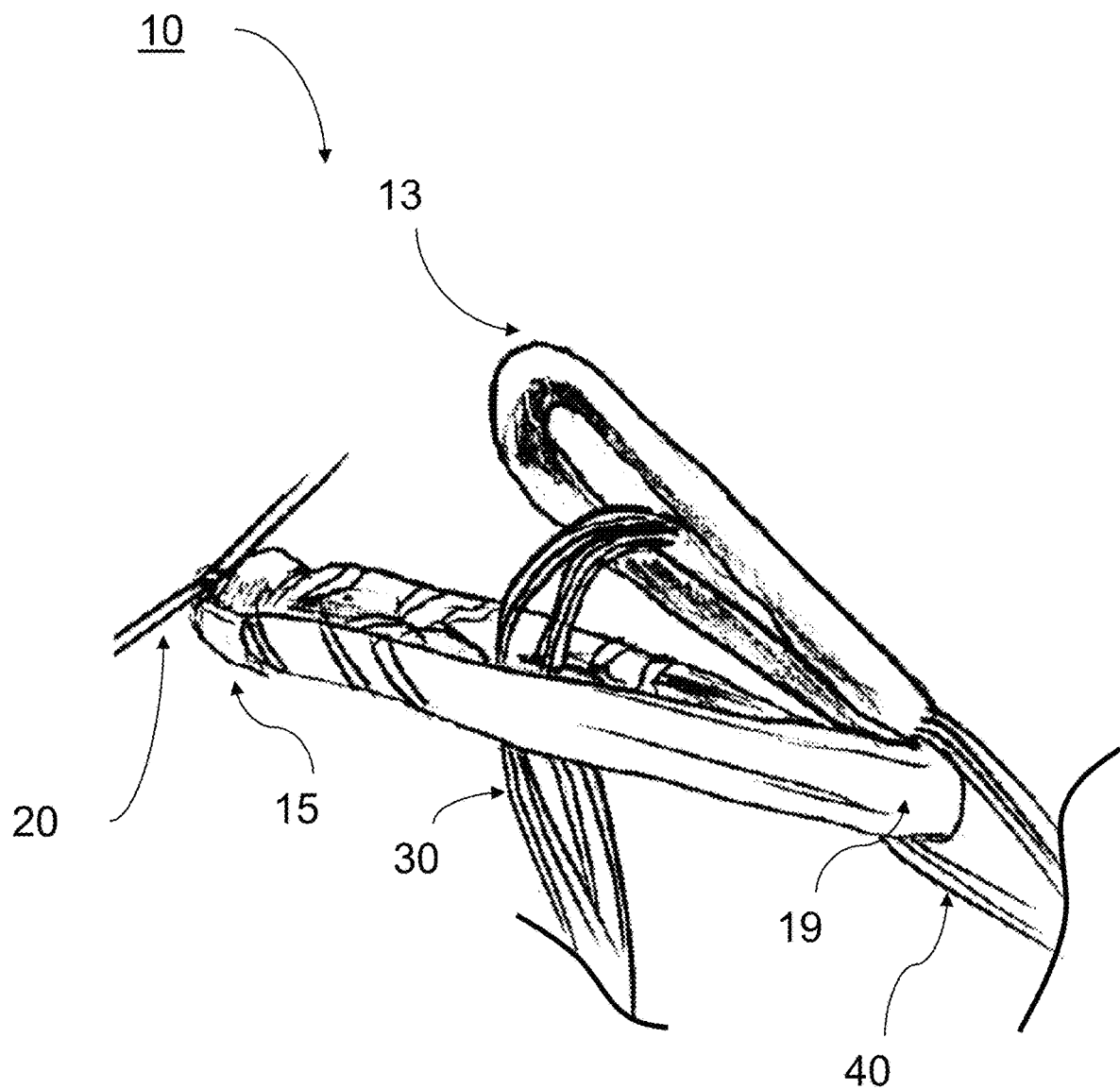
FIG. 8 depicts an example step of a method of this disclosure.

FIG. 8 depicts an example step of this disclosure following the step of FIG. 7. In particular, FIG. 8 shows graft ends 13, 15 being drawn together by implant 30. Implant 30 is depicted having been interwoven with central region 19 that is disposed between ends 13, 15 of graft 10. Sutures 20 can also be seen stitching graft 10 together at end 15 through a plurality of half-stiches (e.g., at least five half-stitches are contemplated though fewer or more half-stitches can be used).

Figure 9:
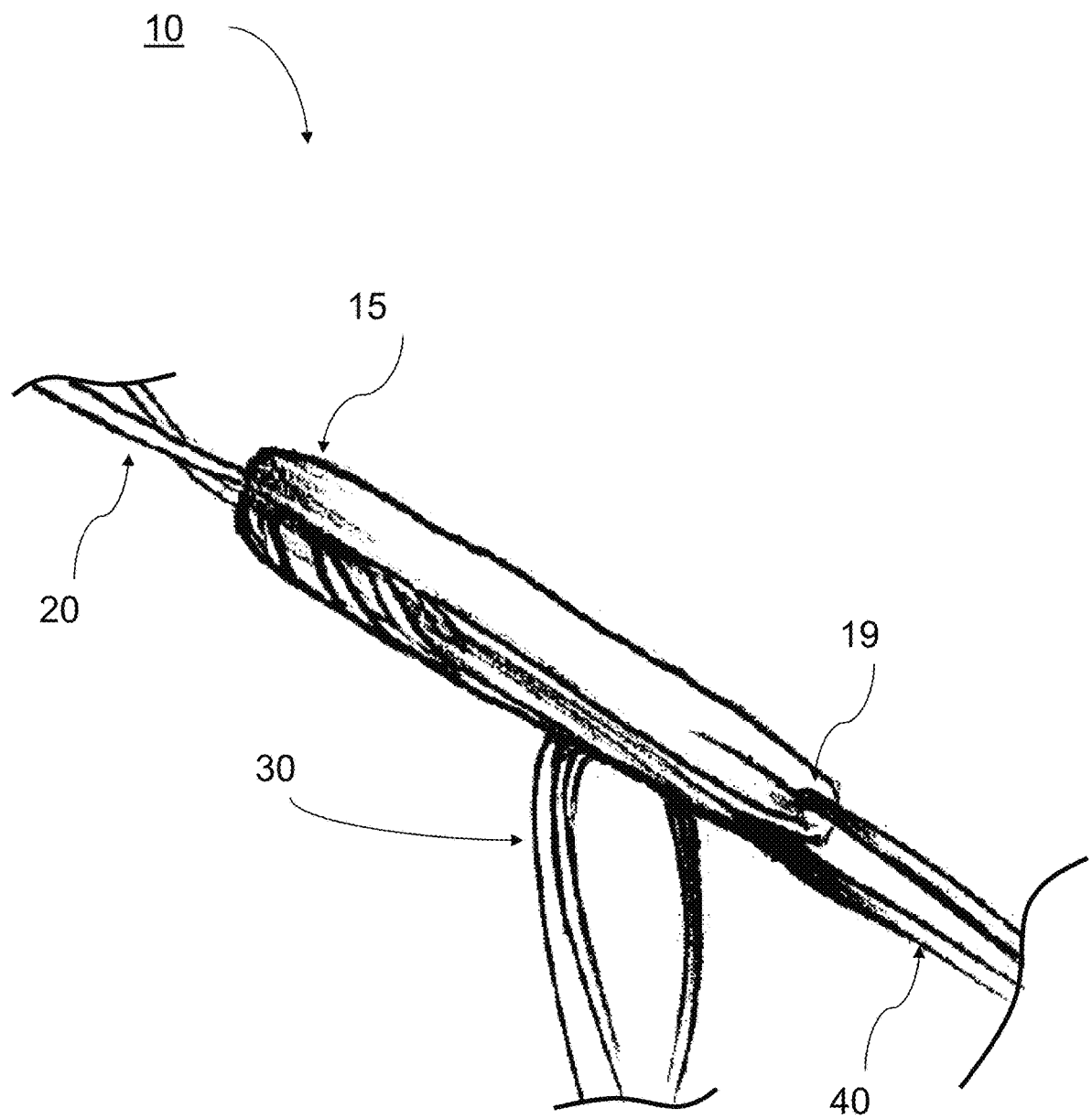
FIG. 9 depicts an example step of a method of this disclosure.

FIG. 9 depicts an example step of this disclosure following the step of FIG. 8. In particular, FIG. 9 shows end 15 remaining in communication with corresponding end 13 being sutured together. Implant 30 is now oriented downwards looped between folded portions of graft. In some examples, implant 30 is oriented in a folded loop with respect to portion 19 whereby the sutured end of graft 10 tucked in the folded loop.

Figure 10:
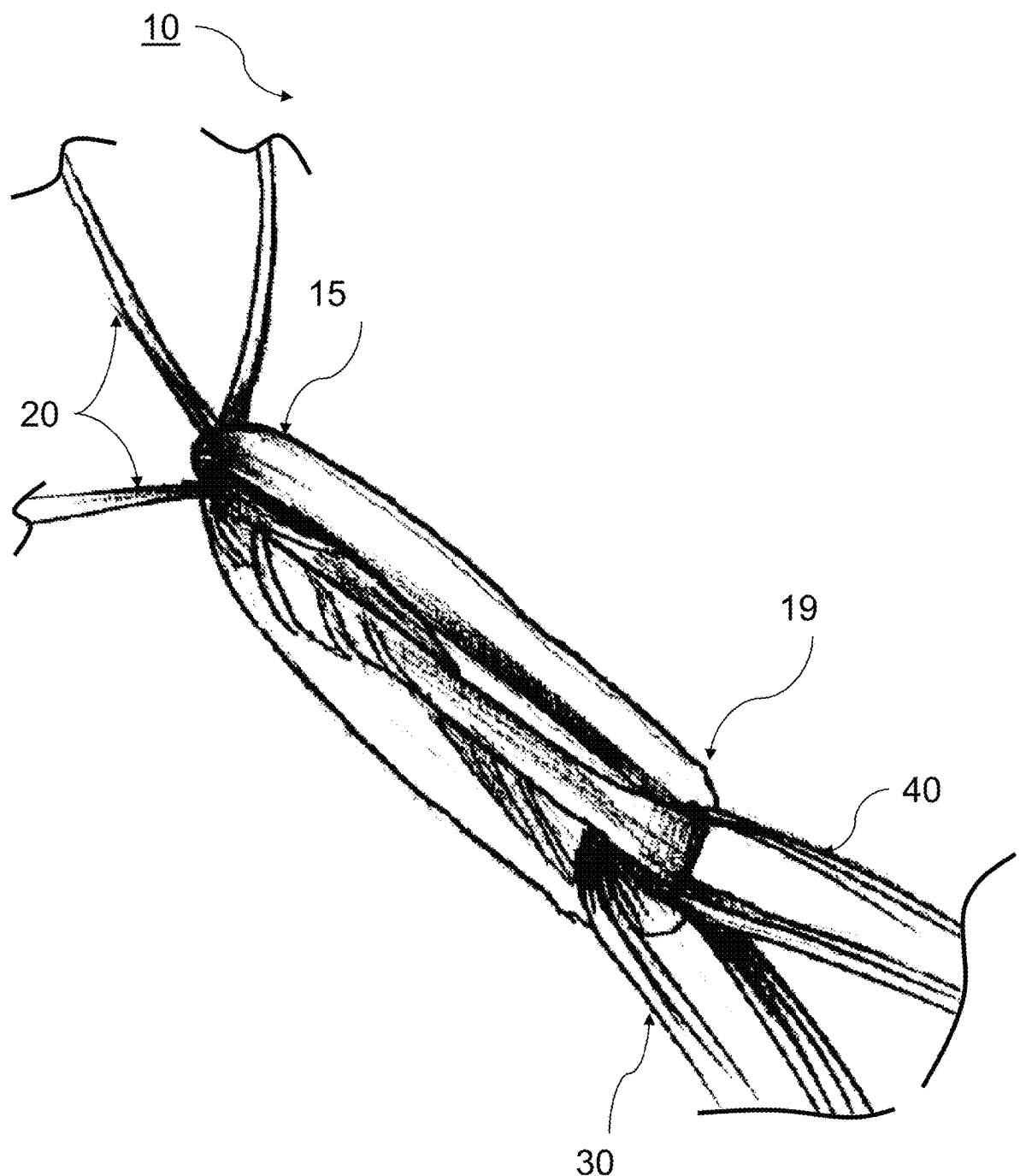
FIG. 10 depicts an example step of a method of this disclosure.

FIG. 10 depicts an example step of this disclosure following the step of FIG. 9. In particular, FIG. 10 shows implant 30 continuing to be drawn through the loop between end 15 and portion 19 until implants 30 and 40 are in communication or otherwise adjacent the other at portion 19. On the opposite end 15, graft 10 is sutured along the outer surface of the folded loop of FIG. 9 at end 15 along with the plurality of previously discussed altering half-stitches (e.g., five altering half-stitches). In some examples, suture tails for final implementation can be left on the distal end in the depicted step of FIG. 10. In some examples, the suture can be cut to leave a suture tail of some predetermined length (e.g., 2 mm length suture tail).

Figure 11:
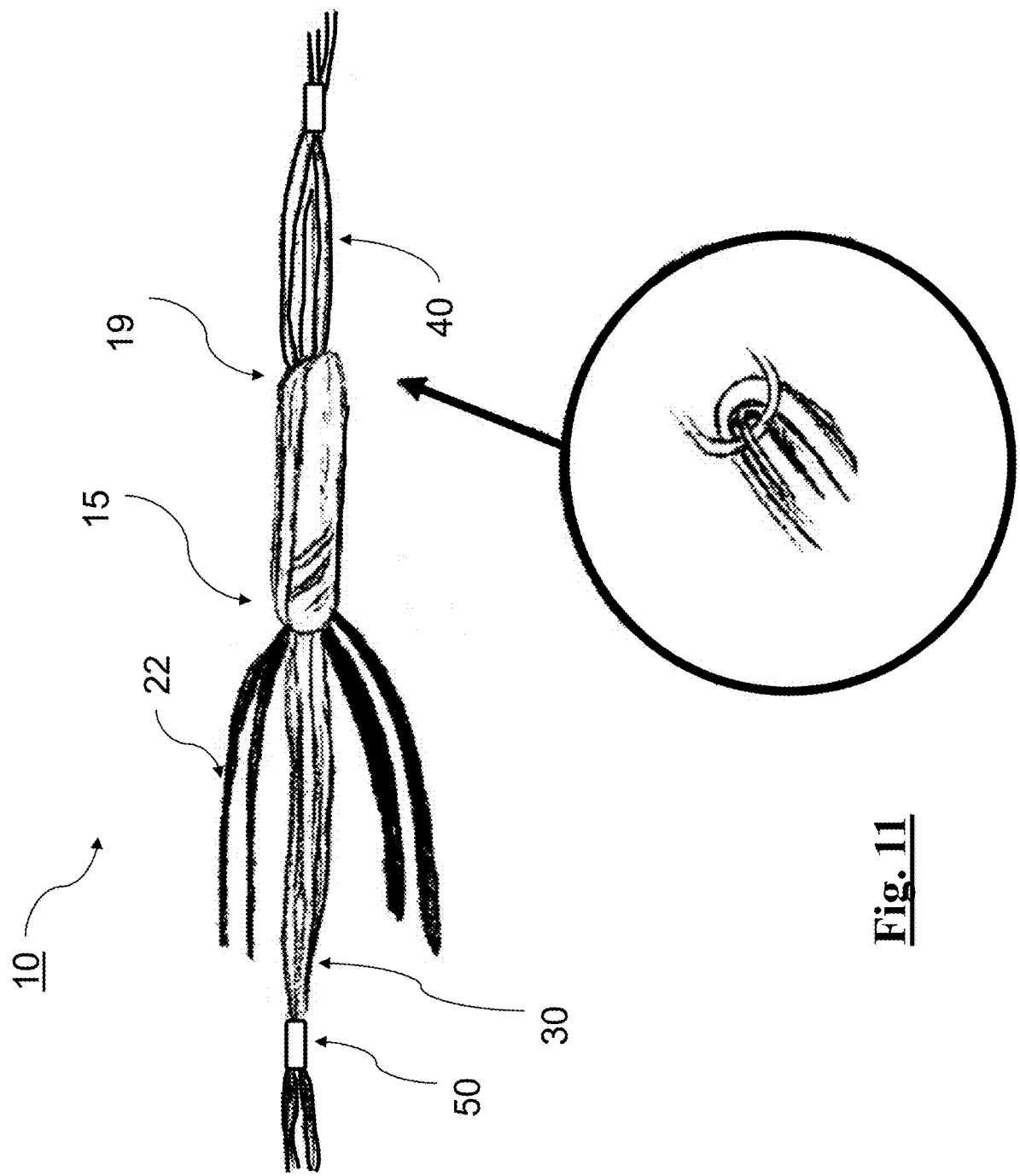
FIG. 11 depicts an example step of a method of this disclosure.

FIG. 11 depicts an example step of this disclosure following the step of FIG. 10. In particular, FIG. 11 shows graft 10 now having undergone at least two folds with implant 30 transitioned back towards end 15 and implant 40 remaining disposed at or adjacent portion 19. In some examples, graft 10 will have been double folded using only two implants (e.g., implant 30 and 40) though fewer or greater number of implants are contemplated for use with the herein disclosed method.

Figure 12:
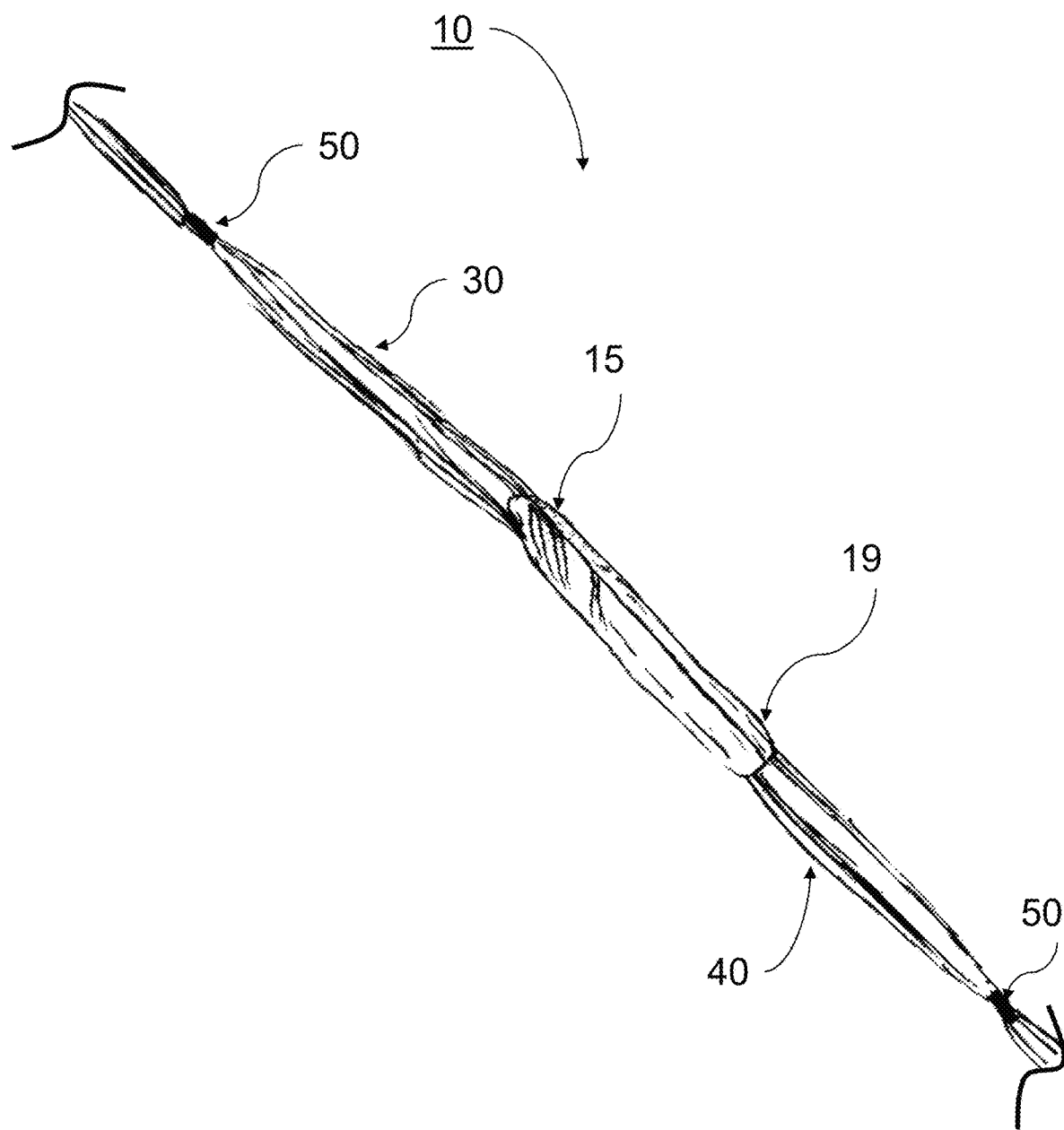
FIG. 12 depicts an example step of a method of this disclosure.

FIG. 12 depicts an example step of this disclosure following the step of FIG. 11. In particular, FIG. 12 shows graft 10 having been double folded with a closed suture graft having two implants (e.g., device 50) with suture tape tails. In some examples, suture tape (e.g., of approximately 1.5 mm) can be passed therethrough into superior leading implant (e.g., femur).

Figure 13:
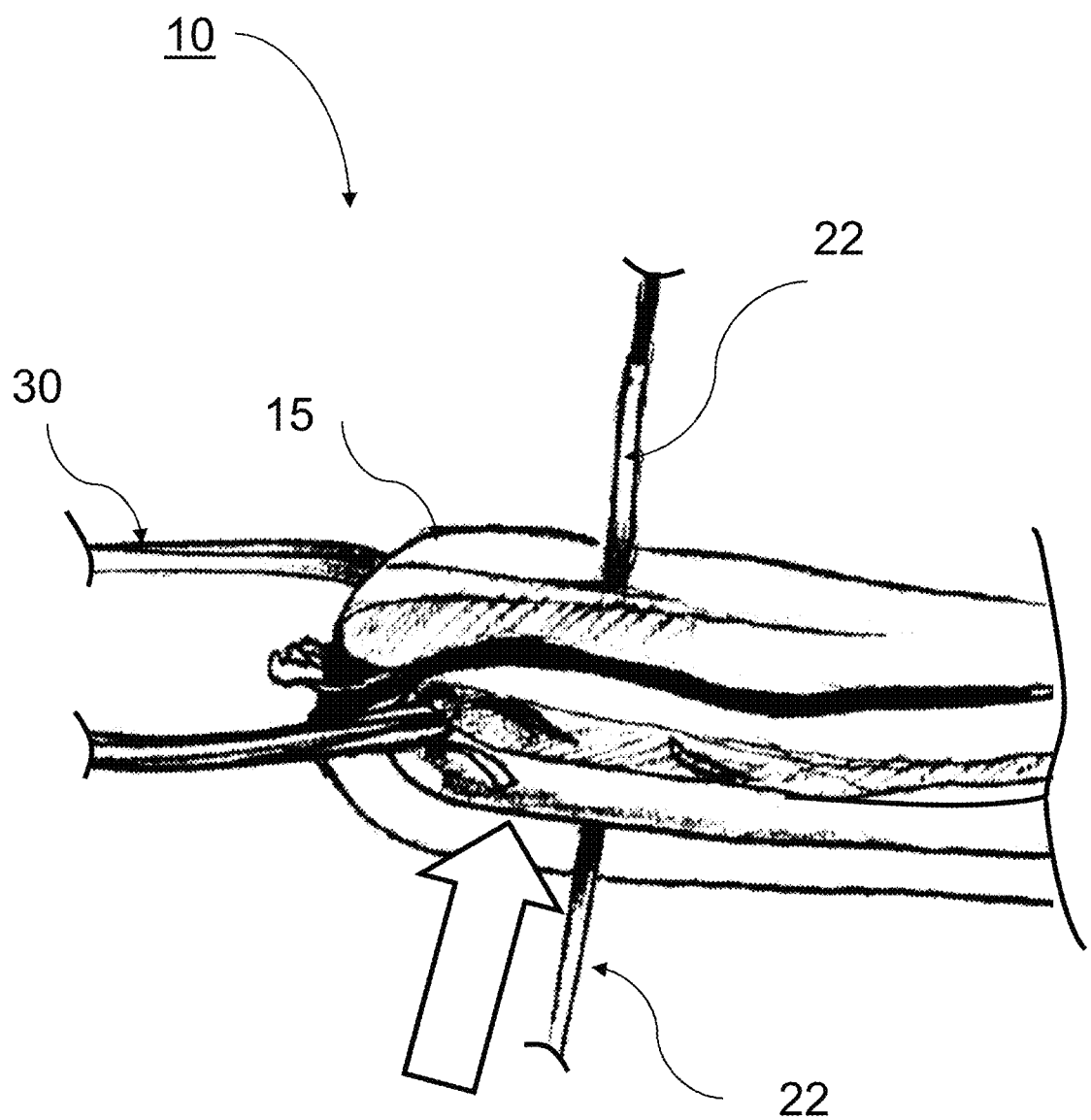
FIG. 13 depicts an example step of a method of this disclosure.

FIG. 13 depicts an example step of this disclosure following the step of FIG. 12. In particular, FIG. 13 shows suture tape 22, which is similar to previously discussed tape 20, inserted with graft 10. Tape 22 can be inserted, for example, with a needle (e.g., a curved needle, a straight needle, etc.) from underneath graft 10 and inserted through one of the inner folded portions of graft 10 in the direction of the depicted arrow.

Figure 14:
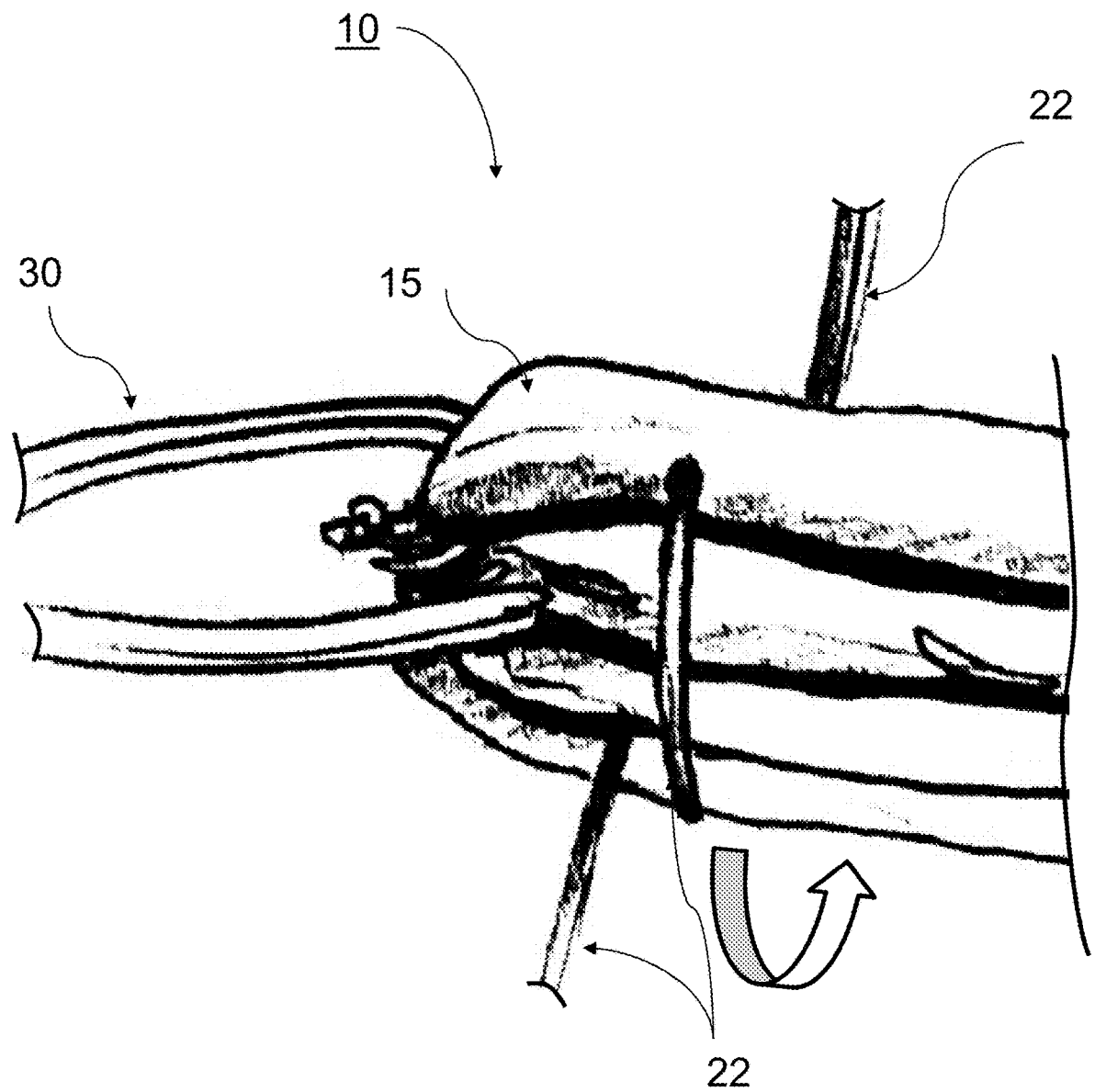
FIG. 14 depicts an example step of a method of this disclosure.

FIG. 14 depicts an example step of this disclosure following the step of FIG. 13. In particular, FIG. 14 shows tape 22 having been looped around graft 10 thereby bypassing the outer loop of graft 10 in the direction of the depicted arrow. The tape 22 is thereafter passed around the outer surface of graft 10.

Figure 15:
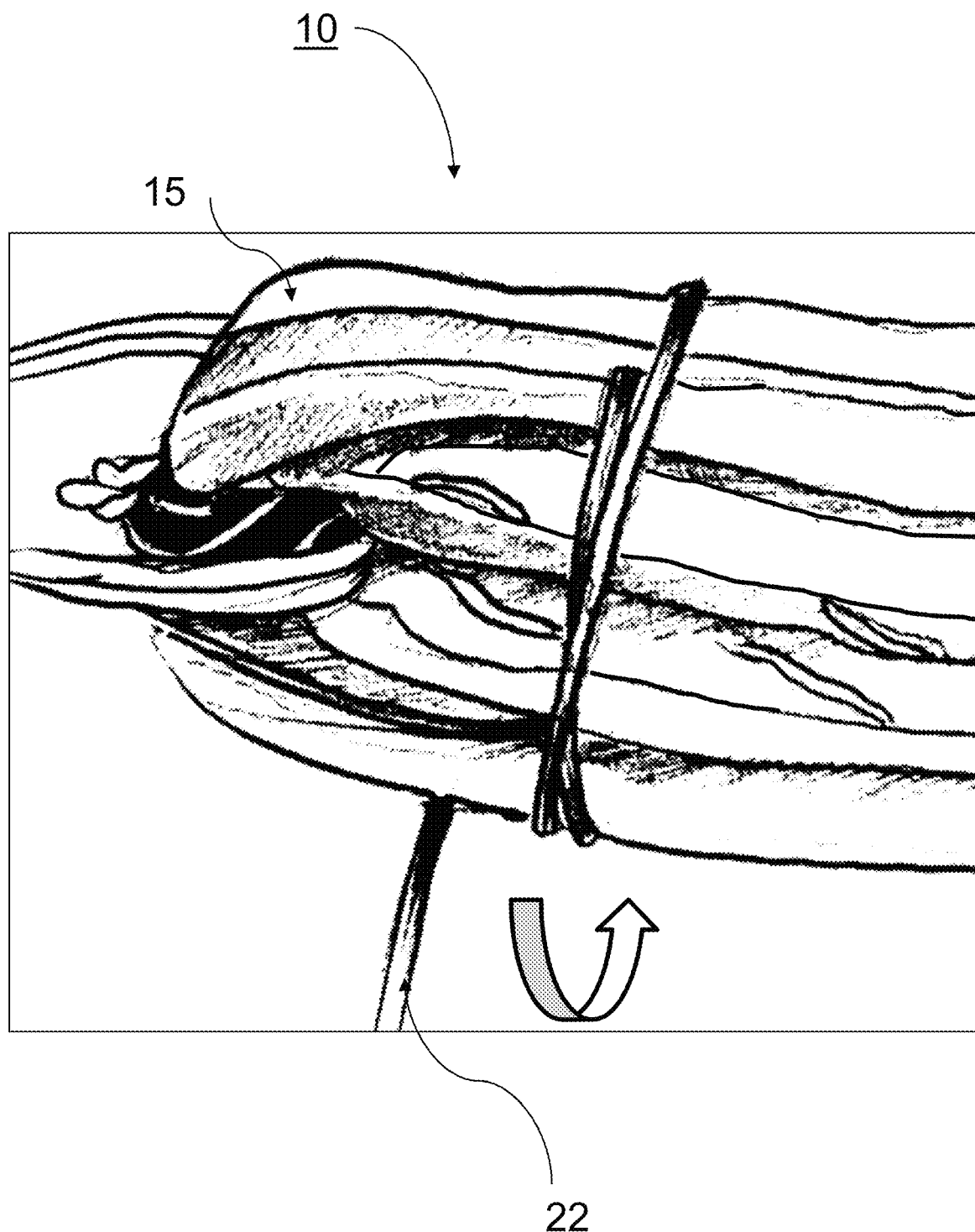
FIG. 15 depicts an example step of a method of this disclosure.

FIG. 15 depicts an example step of this disclosure following the step of FIG. 14. In particular, FIG. 15 shows tape 22 now having been wrapped around graft 10 multiple times, including all folds and intervening sections of graft 10 disposed therein. A needle can now be inserted through the outer most loop of graft 10 in order to terminate on an original insert point.

Figure 16:
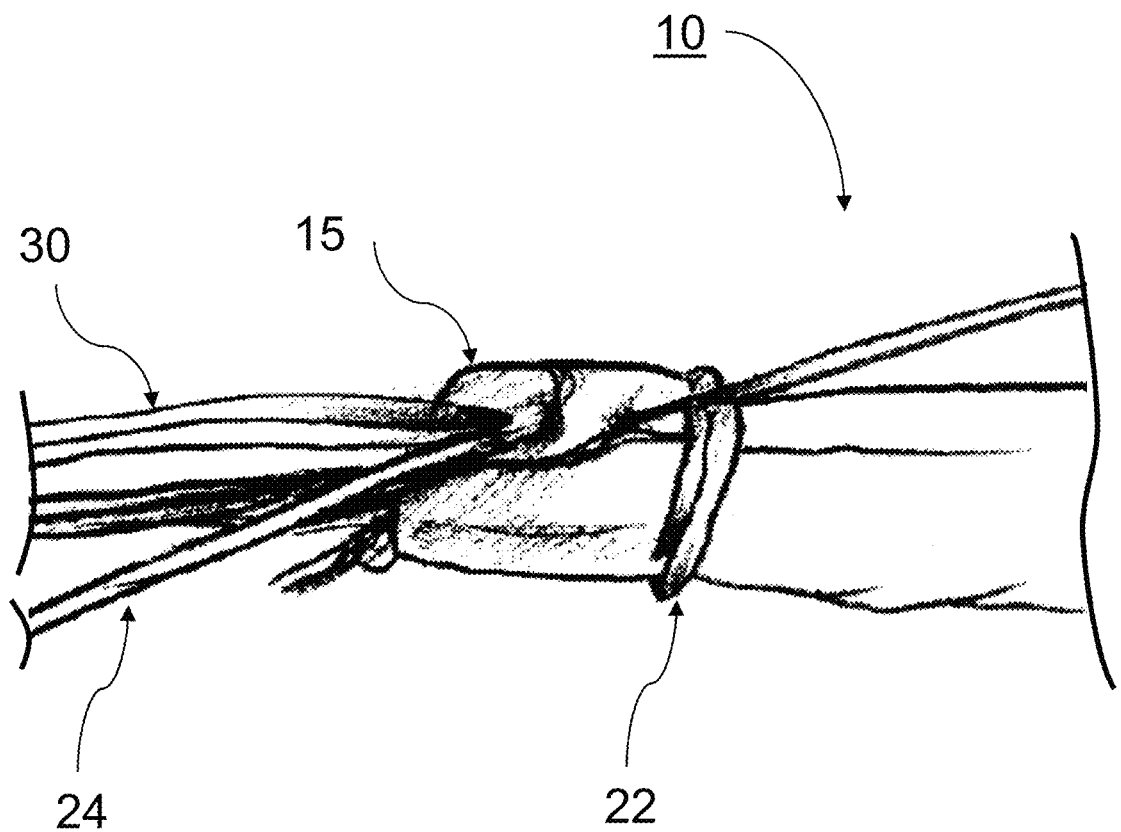
FIG. 16 depicts an example step of a method of this disclosure.

FIG. 16 depicts an example step of this disclosure following the step of FIG. 15. In particular, FIG. 16 shows a final lock suture 24 performed with a plurality of half-stitches (e.g., five alternating half-stitches) after a needle has been inserted as described in FIG. 15. However, the step of FIG. 16 is not so limited and any number of alternating half-stitches can be used as needed or required with graft 10.

Figure 17:
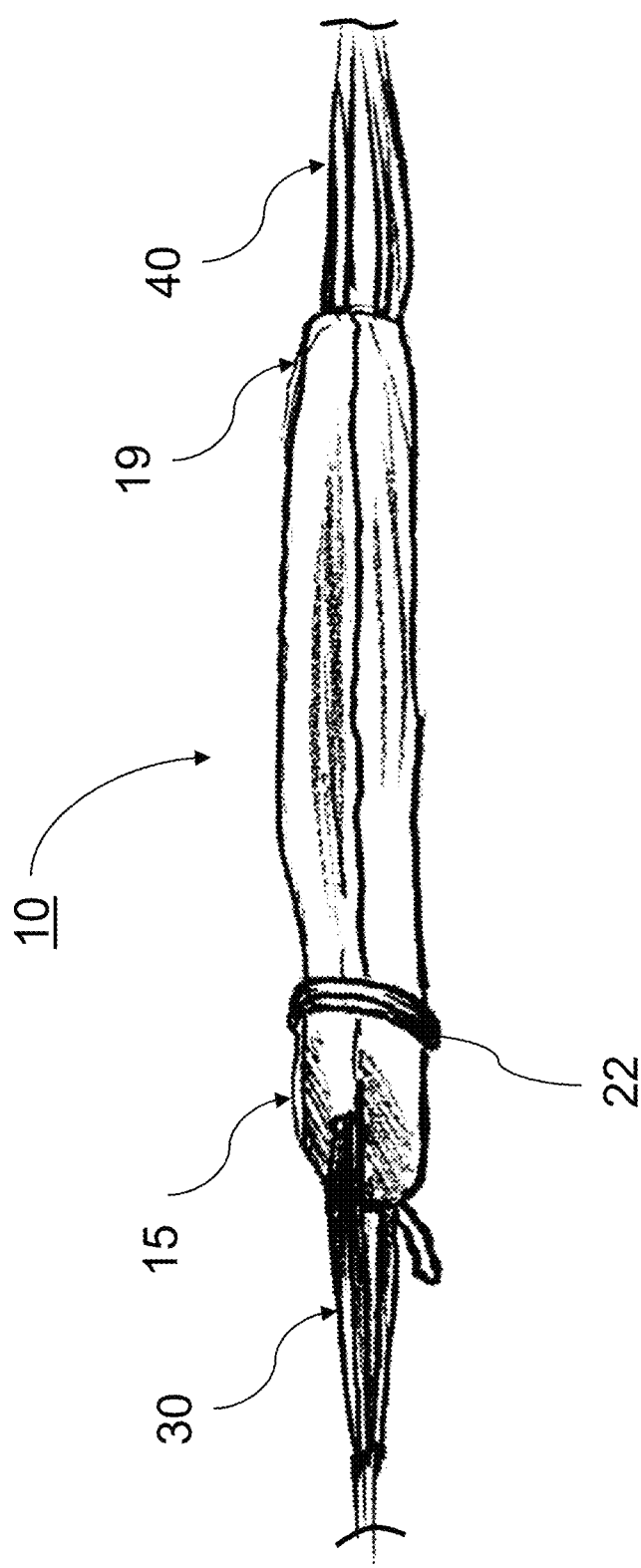
FIG. 17 depicts an example step of a method of this disclosure.

FIG. 17 depicts an example step of this disclosure following the step of FIG. 16. In particular, FIG. 17 depicts an example final step of the method shown in FIGS. 1-17 whereby graft 10 now operatively includes each of its implants 30, 40 secured to respective ends 15, 19 therein, and graft 10 otherwise oriented with one or more folds, and the terminating suture(s) as described in this disclosure.

Figure 18:
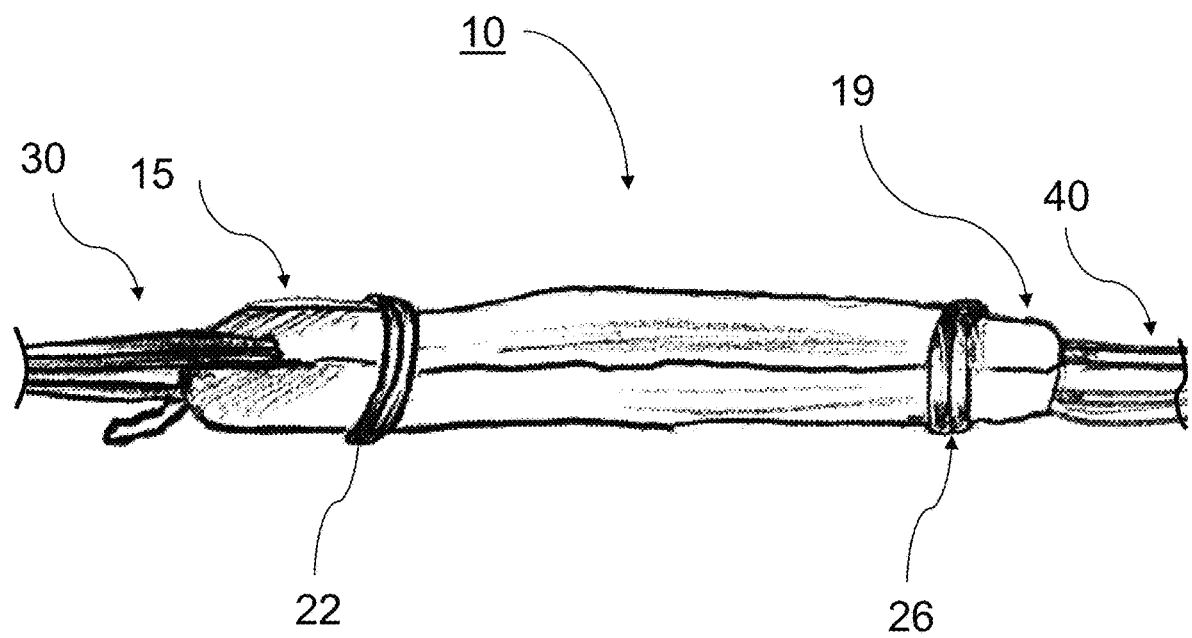
FIG. 18 depicts an example step of a method of this disclosure.

FIG. 18 depicts an example step of this disclosure following the step of FIG. 17. In particular, FIG. 18 depicts an example optional final step of the method shown in FIGS. 1-17 whereby graft 10 now operatively includes each of its implants 30, 40 secured to respective ends 15, 19 therein, and graft 10 otherwise oriented with one or more folds, and an optional suture tape 26 positioned at, adjacent, or otherwise about end 19.

Turning to FIG. 19, an example method 1900 is depicted for preparing a graft for a patient at a location that is separate from an operating room or a hospital. The method 1900 can include 1905 suturing a first proximal end and suturing a first distal end of a graft; 1910 positioning a first implant between the first proximal and first distal ends, the first implant comprising a loop oriented about the graft between the proximal and distal ends; then 1915 folding the first distal or first proximal end of the graft about the loop of the first implant until the first distal or proximal end are in contact or adjacent the other of the ends, wherein a second proximal end and a second distal end are now formed by the folding of the graft, the second proximal end being adjacent the first proximal and distal ends; then 1920 positioning a second implant between the second proximal and second distal ends, the second implant comprising a loop oriented about the graft between the second proximal and distal ends; then 1925 folding the second distal end of the graft about the loop of the second implant until the second distal end contacts or is adjacent the first proximal and/or distal end; then 1930 moving the second distal end away from the first proximal and/or distal end; then 1935 distally moving the first implant towards the second implant and orienting downward the loop of the first implant, the first implant being distally moved between folded segments of the graft; and then 1945 stitching and/or suturing portions of second proximal and/or distal ends together.

Figure 20:
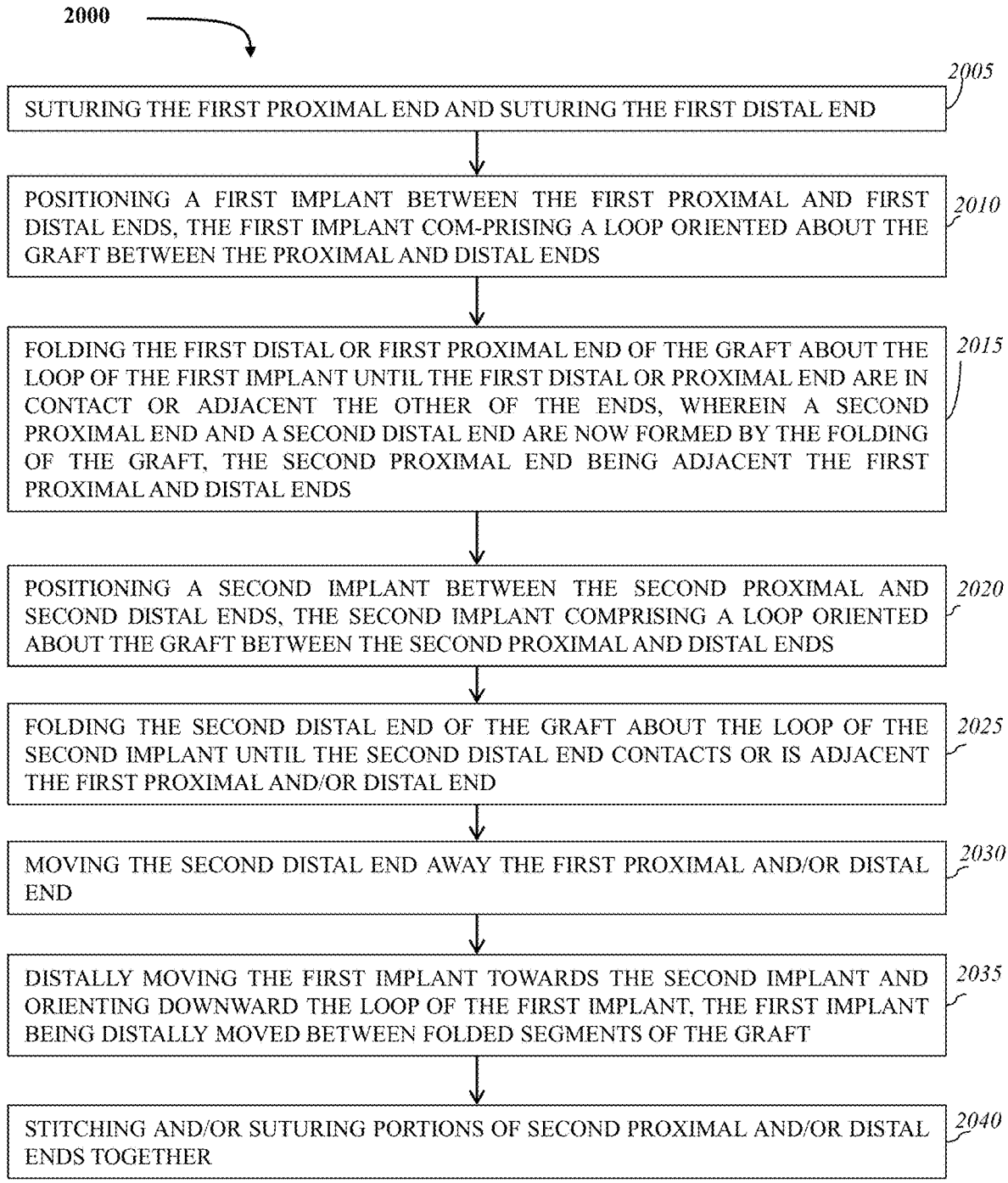
FIG. 20 depicts an example s method of this disclosure.

Turning to FIG. 20, an example method 2000 is depicted for preparing a graft for a patient at a location that is separate from an operating room or a hospital. The method 2000 can include 2005 suturing a first proximal end and suturing a first distal end of a graft; 2010 positioning a first implant between the first proximal and first distal ends, the first implant comprising a loop oriented about the graft between the proximal and distal ends; 2015 folding the first distal or first proximal end of the graft about the loop of the first implant until the first distal or proximal end are in contact or adjacent the other of the ends, wherein a second proximal end and a second distal end are now formed by the folding of the graft, the second proximal end being adjacent the first proximal and distal ends; 2020 positioning a second implant between the second proximal and second distal ends, the second implant comprising a loop oriented about the graft between the second proximal and distal ends; 2025 folding the second distal end of the graft about the loop of the second implant until the second distal end contacts or is adjacent the first proximal and/or distal end; 2030 moving the second distal end away from the first proximal and/or distal end; 2035 distally moving the first implant towards the second implant and orienting downward the loop of the first implant, the first implant being distally moved between folded segments of the graft; and 2040 stitching and/or suturing portions of second proximal and/or distal ends together.

In some examples, method 1900 and/or method 2000 can further include embedding and/or soaking the graft with platelet rich plasma, amnion, growth factors, cytokines, chemokines, or the like. In some examples, the graft can be soaked and/or embedded with growth factors found in amniotic fluid that support cell proliferation and migration across defects and can work with a patient's cells to modulate tissue reconstruction and/or minimize scar formation.

In some embodiments, a method of this disclosure includes some or all steps disclosed for preparing a graft for a patient at a location that is separate from an operating room or a hospital. On some embodiments, the prepared graft 10 of this disclosure are prepared, then stored at freezing temperature (e.g., −80° C.) and maintained frozen until processing for use. In some examples, post-freezing processing can include thawing, cleaning, disinfection, and terminal sterilization following packaging according, and/or being maintained relatively moist. Further, in some examples, the duration of the procedure associated with either steps of FIGS. 1-16 or FIG. 1—can last approximately 30 minutes, though less or more time is contemplated as needed or required.

Further, relevant literature has suggested that example ligaments, such as the anterior cruciate ligament (ACL) or posterior cruciate ligament (PCL), can experience maximum loads between 432 N and 320 N, respectively. Grood, E. S., and F. R. Noyes. "Cruciate Ligament Prosthesis: Strength, Creep, and Fatigue Properties." J Bone Joint Surg Am 58.8 (1976): 1083-8; Kennedy, J. C., et al. "Tension Studies of Human Knee Ligaments. Yield Point, Ultimate Failure, and Disruption of the Cruciate and Tibial Collateral Ligaments." J Bone Joint Surg Am 58.3 (1976): 350-5; and Trent, P. S., P. S. Walker, and B. Wolf. "Ligament Length Patterns, Strength, and Rotational Axes of the Knee Joint." Clin Orthop Relat Res. 117 (1976):263-70. With these load ranges in mind, grafts 10 of this disclosure are contemplated to both exceed the load requirements of these ligaments and do so in an economic, repeatable, and safe environment outside of the hospital setting. In some embodiments, the graft 10 can have an average yield load of 1000 N, 900 N, 800 N, 700 N, and/or 600 N. However, these load values are strictly exemplary values and any other value or range of strength values of graft 10 is contemplated.

It must also be noted that, as used in the specification and the appended claims, the singular forms "a," "an" and "the" include plural referents unless the context clearly dictates otherwise. Ranges may be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the present disclosure. Similarly, it is also to be understood that the mention of one or more components in a device or system does not preclude the presence of additional components or intervening components between those components expressly identified.

Some references, which may include various patents, patent applications, and publications, are cited in a reference list and discussed in the disclosure provided herein. The citation and/or discussion of such references is provided merely to clarify the description of the present disclosure and is not an admission that any such reference is "prior art" to any aspects of the present disclosure described herein. In terms of notation, "[n]" corresponds to the nth reference in the list. All references cited and discussed in this specification are incorporated herein by reference in their entireties and to the same extent as if each reference was individually incorporated by reference.

The descriptions contained herein are examples illustrating the solution and are not intended to limit the scope. As described herein, the solution contemplates many variations and modifications of a system, device, and/or method that can be used to analyze one or more clots and individualize treatment based on the analysis. Variations can include but are not limited to alternative geometries of elements and components described herein, utilizing any of numerous materials for each component or element, utilizing additional components, utilizing additional components to perform functions described herein, or utilizing additional components to perform functions not described herein, for example.

The specific configurations, choice of materials and the size and shape of various elements can be varied according to particular design specifications or constraints requiring a system or method constructed according to the principles of the disclosed technology. Such changes are intended to be embraced within the scope of the disclosed technology. The presently disclosed embodiments, therefore, are considered in all respects to be illustrative and not restrictive. It will therefore be apparent from the foregoing that while particular forms of the disclosure have been illustrated and described, various modifications can be made without departing from the spirit and scope of the disclosure and all changes that come within the meaning and range of equivalents thereof are intended to be embraced therein.

Additional Clauses

The following are additional clauses relative to the present disclosure, which could be combined and/or otherwise integrated with any of the embodiments described above or listed in the claims below.

1. A method for preparing a graft for a patient at a location that is separate from an operating room or a hospital, the method comprising:
   suturing a first proximal end and a first distal end of a tendon;
   positioning a first implant between the first proximal and first distal ends, the first implant comprising a loop oriented about the graft between the proximal and distal ends; then
   folding the first distal or first proximal end of the graft about the loop of the first implant until the first distal or proximal end are in contact or adjacent the other of the ends, wherein a second proximal end and a second distal end are now formed by the folding of the graft, the second proximal end being adjacent the first proximal and distal ends; then
   positioning a second implant between the second proximal and second distal ends, the second implant comprising a loop oriented about the graft between the second proximal and distal ends; then
   folding the second distal end of the graft about the loop of the second implant until the second distal end contacts or is adjacent the first proximal and/or distal end; then
   moving the second distal end away from the first proximal and/or distal end; then
   distally moving the first implant towards the second implant and orienting downward the loop of the first implant, the first implant being distally moved between folded segments of the graft; then
   stitching and/or suturing portions of second proximal and/or distal ends together.

2. The method according to Clause 1, further comprising then transporting the prepared graft to a hospital.

3. The method according to Clause 2, further comprising:
   administering cephalexin to the patient; and
   then reconstructing a treatment site of interest of the patient with the prepared graft.

4. The method according to Clause 3, wherein the cephalexin is orally administered using a capsule equivalent to 250 mg cephalexin.
5. The method according to Clause 3, wherein the cephalexin is orally administered using a capsule equivalent to 500 mg cephalexin.
6. The method according to Clause 3, wherein the cephalexin is orally administered using a capsule equivalent to 700 mg cephalexin.
7. The method according to Clause 2, further comprising:
    administering Keflex, ancef via intravenous therapy, and/or Clindamycin to the patient; and then
    reconstructing a treatment site of interest of the patient with the prepared graft.
8. The method according to Clause 1, wherein a duration of time to perform each step of the method is approximately 30 minutes.
9. The method according to Clause 1, wherein a step of providing the graft relates to one or more tendons from the semitendinosus.
10. The method according to Clause 1, wherein a step of providing the graft relates to one or more tendons from the gracilis.
11. The method according to Clause 1, wherein a step of providing the graft relates to one or more tendons from the anterior tibialis.
12. The method according to Clause 1, wherein a step of providing the graft relates to one or more tendons from the posterior tibialis.
13. The method according to Clause 1, wherein a step of providing the graft relates to one or more tendons from the peroneus longus.
14. The method according to Clause 1, wherein the step of suturing the first proximal end and suturing the first distal end is implemented using the Krackow method.
15. The method according to Clause 1, wherein the step of suturing the first proximal end and suturing the first distal end is implemented using suture tape of 1.5 mm and/or 2.0 mm.
16. The method according to Clause 1, wherein the step of moving the second distal end away from the first proximal and/or distal end is implemented by pivoting the second distal end about a pivot point between the second distal end and the first proximal and/or distal end.
17. The method according to Clause 1, wherein the step of moving the second distal end away from the first proximal and/or distal end is implemented by pivoting the second distal end a predetermined distance away from the first proximal and/or distal end, the predetermined distance being greater than a width of the first implant.
18. The method according to Clause 1, wherein the step of moving the second distal end away from the first proximal and/or distal end is implemented by pivoting the second distal end a predetermined distance away from the first proximal and/or distal end, the predetermined distance being greater than a thickness of the first implant.
19. The method according to Clause 1, wherein the first and second implants comprise one or more durable elongate ropes constructed from a high tension biocompatible material.
20. The method according to Clause 1, wherein the step of orienting downward the loop of the first implant comprises reorienting the first implant at least 90 degrees until being positioned by having its loop angled substantially downward.
21. The method according to Clause 1, wherein the step of stitching and/or suturing portions of second proximal and/or distal ends together further comprises implanting at least five half-stiches.
22. The method according to Clause 1, wherein the graft measures 230 mm-260 mm length by 8.5 mm-10.0 mm.
23. A graft prepared according to any of Clauses 1, wherein the first and second implants comprise one or more durable elongate ropes constructed from a biocompatible material.
24. A graft prepared by folding said graft twice onto itself and interweaving an implant at opposing distal and proximal ends of said double folded graft, the implant constructed from a high tension biocompatible material.
25. The graft according to Clause 24, wherein the graft relates to one or more tendons from the semitendinosus.
26. The graft according to Clause 24, wherein the graft relates to one or more tendons from the gracilis.
27. The graft according to Clause 24, wherein the graft relates to one or more tendons from the anterior tibialis.
28. The graft according to Clause 24, wherein the graft relates to one or more tendons from the posterior tibialis.
29. The graft according to Clause 24, wherein the graft relates to one or more tendons from the peroneus longus.
30. A method for preparing a graft for a patient at a location that is separate from an operating room or a hospital, the method comprising:
    providing a tendon having a first proximal end and a first distal end;
    suturing the first proximal end and suturing the first distal end;
    positioning a first implant between the first proximal and first distal ends, the first implant comprising a loop oriented about the graft between the proximal and distal ends;
    folding the first distal or first proximal end of the graft about the loop of the first implant until the first distal or proximal end are in contact or adjacent the other of the ends, wherein a second proximal end and a second distal end are now formed by the folding of the graft, the second proximal end being adjacent the first proximal and distal ends;
    positioning a second implant between the second proximal and second distal ends, the second implant comprising a loop oriented about the graft between the second proximal and distal ends;
    folding the second distal end of the graft about the loop of the second implant until the second distal end contacts or is adjacent the first proximal and/or distal end;
    moving the second distal end away from the first proximal and/or distal end;
    distally moving the first implant towards the second implant and orienting downward the loop of the first implant, the first implant being distally moved between folded segments of the graft; and
    stitching and/or suturing portions of second proximal and/or distal ends together.
31. The method according to Clause 30, further comprising transporting the prepared graft to a hospital.

32. The method according to Clause 31, further comprising then reconstructing a treatment site of interest of a patient with the prepared graft.

33. Use of a graft prepared for a patient at a location that is separate from an operating room or a hospital, comprising:
suturing a first proximal end and a first distal end of a tendon;
positioning a first implant between the first proximal and first distal ends, the first implant comprising a loop oriented about the graft between the proximal and distal ends; then
folding the first distal or first proximal end of the graft about the loop of the first implant until the first distal or proximal end are in contact or adjacent the other of the ends, wherein a second proximal end and a second distal end are now formed by the folding of the graft, the second proximal end being adjacent the first proximal and distal ends; then
positioning a second implant between the second proximal and second distal ends, the second implant comprising a loop oriented about the graft between the second proximal and distal ends; then
folding the second distal end of the graft about the loop of the second implant until the second distal end contacts or is adjacent the first proximal and/or distal end; then
moving the second distal end away from the first proximal and/or distal end; then
distally moving the first implant towards the second implant and orienting downward the loop of the first implant, the first implant being distally moved between folded segments of the graft; then
stitching and/or suturing portions of second proximal and/or distal ends together;
then transporting the prepared graft to a hospital;
administering cephalexin to the patient; and
then reconstructing a treatment site of interest of a patient with the prepared graft.

34. Use according to Clause 33, wherein the cephalexin is orally administered using a capsule equivalent to 250 mg cephalexin.

35. Use according to Clause 33, wherein the cephalexin is orally administered using a capsule equivalent to 500 mg cephalexin.

36. Use according to Clause 33, wherein the cephalexin is orally administered using a capsule equivalent to 700 mg cephalexin.

37. Use according to Clause 33, wherein the graft relates to one or more tendons from the semitendinosus.

38. Use according to Clause 33, wherein the graft relates to one or more tendons from the gracilis.

39. Use according to Clause 33, wherein the graft relates to one or more tendons from the anterior tibialis.

40. Use according to Clause 33, wherein the graft relates to one or more tendons from the posterior tibialis.

41. Use according to Clause 33, wherein the graft relates to one or more tendons from the peroneus longus.

42. Use according to Clause 33, wherein the step of suturing the first proximal end and suturing the first distal end is implemented using the Krackow method.

43. Use according to Clause 33, wherein the step of suturing the first proximal end and suturing the first distal end is implemented using suture tape of 1.5 mm and/or 2.0 mm.

44. Use according to Clause 33, wherein the step of moving the second distal end away from the first proximal and/or distal end is implemented by pivoting the second distal end about a pivot point between the second distal end and the first proximal and/or distal end.

45. Use according to Clause 33, wherein the step of moving the second distal end away from the first proximal and/or distal end is implemented by pivoting the second distal end a predetermined distance away from the first proximal and/or distal end, the predetermined distance being greater than a width of the first implant.

46. Use according to Clause 33, wherein the step of moving the second distal end away from the first proximal and/or distal end is implemented by pivoting the second distal end a predetermined distance away from the first proximal and/or distal end, the predetermined distance being greater than a thickness of the first implant.

47. Use according to Clause 33, wherein the first and second implants comprise one or more durable elongate ropes constructed from a high tension biocompatible material.

48. Use according to Clause 33, wherein the step of orienting downward the loop of the first implant comprises reorienting the first implant at least 90 degrees until being positioned by having its loop angled substantially downward.

49. Use according to Clause 33, wherein the step of stitching and/or suturing portions of second proximal and/or distal ends together further comprises implanting at least five half-stiches.

50. Use according to Clause 33, wherein the graft measures 230 mm-260 mm length by 8.5 mm-10.0 mm.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:

1. A method for preparing a graft for a patient at a location that is separate from an operating room or a hospital, the method comprising:
suturing a first proximal end and a first distal end of a tendon;
positioning a first implant between the first proximal and first distal ends, the first implant comprising a loop oriented about the graft between the proximal and distal ends; then
folding the first distal or first proximal end of the graft about the loop of the first implant until the first distal or proximal end are in contact or adjacent the other of the ends, wherein a second proximal end and a second distal end are now formed by the folding of the graft, the second proximal end being adjacent the first proximal and distal ends; then
positioning a second implant between the second proximal and second distal ends, the second implant comprising a loop oriented about the graft between the second proximal and distal ends; then
folding the second distal end of the graft about the loop of the second implant until the second distal end contacts or is adjacent the first proximal and/or distal end; then
moving the second distal end away from the first proximal and/or distal end; then distally moving the first implant towards the second implant and orienting downward the loop of the first implant, the first implant being distally moved between folded segments of the graft; then stitching and/or suturing portions of second proximal and/or distal ends together.

2. The method according to claim 1, further comprising then transporting the prepared graft to a hospital.

3. The method according to claim 2, further comprising:
administering cephalexin to the patient; and
then reconstructing a treatment site of interest of a patient with the prepared graft.

4. The method according to claim 3, wherein the cephalexin is orally administered using a capsule equivalent to 250 mg cephalexin.

5. The method according to claim 3, wherein the cephalexin is orally administered using a capsule equivalent to 500 mg cephalexin.

6. The method according to claim 3, wherein the cephalexin is orally administered using a capsule equivalent to 700 mg cephalexin.

7. The method according to claim 2, further comprising:
administering cefazolin via intravenous therapy, and/or Clindamycin to the patient; and then
reconstructing a treatment site of interest of the patient with the prepared graft.

8. The method according to claim 1, wherein a duration of time to perform each step of the method is approximately 30 minutes.

9. The method according to claim 1, wherein a step of providing the graft relates to one or more tendons from the semitendinosus, the gracilis, the anterior tibialis, or the posterior tibialis.

10. The method according to claim 1, wherein a step of providing the graft relates to one or more tendons from the peroneus longus.

11. The method according to claim 1, wherein the step of suturing the first proximal end and suturing the first distal end is implemented using the Krackow method.

12. The method according to claim 1, wherein the step of suturing the first proximal end and suturing the first distal end is implemented using suture tape of 1.5 mm and/or 2.0 mm.

13. The method according to claim 1, wherein the step of moving the second distal end away from the first proximal and/or distal end is implemented by pivoting the second distal end about a pivot point between the second distal end and the first proximal and/or distal end.

14. The method according to claim 1, wherein the step of moving the second distal end away from the first proximal and/or distal end is implemented by pivoting the second distal end a predetermined distance away from the first proximal and/or distal end, the predetermined distance being greater than a width of the first implant.

15. The method according to claim 1, wherein the step of moving the second distal end away from the first proximal and/or distal end is implemented by pivoting the second distal end a predetermined distance away from the first proximal and/or distal end, the predetermined distance being greater than a thickness of the first implant.

16. The method according to claim 1, wherein the first and second implants comprise one or more durable elongate ropes constructed from a high tension biocompatible material.

17. The method according to claim 1, wherein the step of orienting downward the loop of the first implant comprises reorienting the first implant at least 90 degrees until being positioned by having its loop angled substantially downward.

18. The method according to claim 1, wherein the step of stitching and/or suturing portions of second proximal and/or distal ends together further comprises implanting at least five half-stiches.

19. The method according to claim 1, wherein the graft measures 230 mm-260 mm length by 8.5 mm 10.0 mm.

20. A graft prepared according to claim 1, wherein the first and second implants comprise one or more durable elongate ropes constructed from a biocompatible material.

* * * * *